(12) United States Patent
Rosemurgy et al.

(10) Patent No.: US 10,076,229 B2
(45) Date of Patent: Sep. 18, 2018

(54) ENDOSCOPIC OVERTUBE (75) Inventors: Alexander S. Rosemurgy, Tampa, FL (US); Sharona B. Ross, Tampa, FL (US)

(73) Assignee: University of South Florida, Tampa, FL (US)

(*) Notice: Subject to any disclaimer, the term of this patent is extended or adjusted under 35 U.S.C. 154(b) by 493 days.

(21) Appl. No.: 12/840,402

(22) Filed: Jul. 21, 2010

(65) Prior Publication Data

US 2010/0331625 A1 Dec. 30, 2010

Related U.S. Application Data

(63) Continuation of application No. PCT/US2009/031674, filed on Jan. 22, 2009.

(60) Provisional application No. 61/022,655, filed on Jan. 22, 2008.

(51) Int. Cl.
*A61B 1/06* (2006.01)
*A61B 1/00* (2006.01)
*A61B 1/04* (2006.01)
*A61B 1/012* (2006.01)
*A61B 1/31* (2006.01)
*A61B 1/005* (2006.01)

(52) U.S. Cl.
CPC .......... *A61B 1/00082* (2013.01); *A61B 1/005* (2013.01); *A61B 1/00078* (2013.01); *A61B 1/00137* (2013.01); *A61B 1/00154* (2013.01); *A61B 1/012* (2013.01); *A61B 1/31* (2013.01)

(58) Field of Classification Search
CPC .................. A61B 1/00078; A61B 1/00119
USPC .................. 600/113–116, 121–125, 138–140
See application file for complete search history.

(56) References Cited

U.S. PATENT DOCUMENTS

| | | | |
|---|---|---|---|
| 4,406,656 A * | 9/1983 | Hattler et al. | 604/523 |
| 5,297,536 A | 3/1994 | Wilk | |
| 5,620,408 A | 4/1997 | Vennes et al. | |
| 5,759,151 A * | 6/1998 | Sturges | 600/139 |
| 5,846,182 A | 12/1998 | Wolcott | |

(Continued)

OTHER PUBLICATIONS

Ceppa et al., Laparoscopic Transgastric Endoscopy After Roux-en-Y Gastric Bypass, Surgery for Obesity and Related Diseases, 2007, vol. 3, pp. 21-24.

(Continued)

*Primary Examiner* — John P Leubecker
*Assistant Examiner* — William Chou
(74) *Attorney, Agent, or Firm* — Nicholas Pfeifer; Smith & Hopen, P.A.

(57) ABSTRACT

An over-tube was developed for receiving and guiding endoscopic instruments into a patient's anus, through the colon, and into the peritoneum. The over-tube has a flexible sheath adapted for insertion into the anus through the colon and out the peritoneum of a patient. A stiffened region is used to protect the colonic wall from injury during insertion of medical instruments through the patient's lower gastro-intestinal tract. The proximal end of the over-tube is surrounded by two narrow inflatable balloons on either side of the colotomy to keep the device in place with its lumen open into the peritoneum and further prevent leakage of insufflation. The device may comprise two channels, one for duel channel endoscopes and larger medical instruments or single lumen endoscopes, and an additional channel for surgical instruments. A distal valve prevents insufflation leakage, making the device especially useful in NOTES surgeries.

20 Claims, 9 Drawing Sheets

(56) References Cited

U.S. PATENT DOCUMENTS

| | | | |
|---|---|---|---|
| 5,916,147 A * | 6/1999 | Boury | 600/139 |
| 5,924,977 A * | 7/1999 | Yabe et al. | 600/121 |
| 6,190,349 B1 | 2/2001 | Ash et al. | |
| 6,328,730 B1 * | 12/2001 | Harkrider, Jr. | 600/130 |
| 6,761,685 B2 | 7/2004 | Adams et al. | |
| 6,793,621 B2 | 9/2004 | Butler et al. | |
| 2001/0000040 A1 * | 3/2001 | Adams et al. | 600/121 |
| 2003/0065359 A1 * | 4/2003 | Weller | A61B 17/0482 606/213 |
| 2004/0034369 A1 * | 2/2004 | Sauer | A61B 1/00071 606/139 |
| 2004/0111020 A1 * | 6/2004 | Long | 600/407 |
| 2005/0070850 A1 * | 3/2005 | Albrecht | A61B 17/34 604/167.03 |
| 2005/0119524 A1 * | 6/2005 | Sekine et al. | 600/114 |
| 2005/0159645 A1 * | 7/2005 | Bertolero et al. | 600/116 |
| 2005/0267335 A1 * | 12/2005 | Okada | A61B 1/0014 600/173 |
| 2006/0089532 A1 * | 4/2006 | Tartaglia et al. | 600/114 |
| 2007/0250038 A1 | 10/2007 | Boulais | |
| 2008/0097152 A1 * | 4/2008 | Stefanchik | A61B 1/00071 600/114 |
| 2008/0262301 A1 | 10/2008 | Gibbons et al. | |
| 2013/0096378 A1 * | 4/2013 | Alexander | A61B 1/00016 600/106 |
| 2013/0253537 A1 * | 9/2013 | Saadat | A61B 17/0401 606/139 |

OTHER PUBLICATIONS

Peters et al., Laparoscopic Transgastric Endoscopic Retrograde Cholangiopancreatography for Benign Common Bile Duct Structure After Roux-en-Y Gastric Bypass, Surgical Endoscopy, 2002, vol. 16, pp. 1106.

Hondo et al., "Transgastricy Access by Balloon Overtube for Intraperitoneal Surgery," Surg. Enclose., 2007, vol. 21, pp. 1867-1869.

Pearl et al., "Natural Orifice Transluminal Endoscopic Surgery: Past, Present and Future," Journal of Minimal Access Surgery, 2007, vol. 3, No. 2, pp. 43-46.

Wagh et al., "Surgery Insight: Natural Orifice Transluminal Endoscopic Surgery—An Analysis of Work to Date," Gastr. & Hept., 2007, vol. 4, No. 7, pp. 386-392.

International Preliminary Report on Patentability for application No. PCT/US2009/031674, dated Jan. 22, 2008.

Litynski. 1999. "Endoscopic Surgery: The History, the Pioneers." World J. Surg. vol. 23. pp. 745-753.

Jagannath et al. 2005. "Peroral Transgastric Endoscopic Ligation of Fallopian Tubes with Long-Term Survival in a Porcine Model." Gastrointestinal Endoscopy. vol. 61. No. 3. pp. 449-453.

Park et al. 2005. "Experimental Studies of Transgastric Gallbladder Surgery: Cholecystectomy and Cholecystogastric Anastomosis." Gastrointestinal Endoscopy. vol. 61. No. 4. pp. 601-606.

Wagh et al. 2006. "Survival Studies After Endoscopic Transgastric Oophorectomy and Tubectomy in a Porcine Model." Gastrointestinal Endoscopy. vol. 63. No. 3. pp. 473-478.

Merrifield et al. 2006. "Pereral Transgastric Organ Resection: a Feasibility Study in Pigs." Gastrointestinal Endoscopy. vol. 63. No. 4. pp. 693-697.

Kantsevoy et al. 2006. "Transgastric Endoscopic Splenectomy Is It Possible?" Surg. Endosc. vol. 20. pp. 522-525.

Hochberger et al. 2005. "Transgastric Surgery in the Abdomen: the Dawn of a New Era?" Gastrointestinal Endoscopy. vol. 62. No. 2. pp. 293-296.

* cited by examiner

ENDOSCOPIC OVERTUBE

CROSS REFERENCE TO RELATED APPLICATIONS

This application is a continuation of prior filed International Application, Serial Number PCT/US2009/031674 filed Jan. 22, 2009, which claims priority to U.S. provisional patent application No. 61/022,655 filed Jan. 22, 2008 which is hereby incorporated by reference into this disclosure.

FIELD OF INVENTION

This invention relates to surgical intubation. More specifically, the invention is an over-tube for endoscopic and minimally invasive surgery.

BACKGROUND OF THE INVENTION

Laparoscopic surgical techniques have been developed in order to avoid large skin incisions associated with traditional surgery. Such minimally invasive surgical techniques have been evolving for more than 100 years, since Georg Kelling performed the first experimental laparoscopy in 1901. (Litynski, G. Endoscopic surgery, the history, the pioneers. World J. Surg. 1999 August; 23(8):745-53). Currently, hybrid procedures combining flexible endoscopy and laparoscopy, such as intraoperative enteroscopy and laparoscopic-assisted endoscopic retrograde cholangiopancreatography, are performed in increasing numbers. (Ceppa, F., et al. Laparoscopic transgastric endoscopic retrograde endoscopy after Roux-en-Y gastric bypass. Surg. Obes. Relat. Dis. 3: 21-24 2007; Peters, M., et al. Laparoscopic transgastric endoscopic retrograde cholangiopancreatography for benign common bile duct structure after Roux-en-Y gastric bypass. Surg. Endosc. 16:1106 2002).

Recently, natural orifice transluminal endoscopic surgery (NOTES) has been performed by entering the peritoneal cavity via the stomach, colon, vagina, or bladder. (Pearl, J., Ponsky, J., Natural orifice transluminal endoscopic surgery: past present and future. J Min. Acc. Surg. 3:2 43-46 2008; Wilk, P., U.S. Pat. No. 5,297,536). NOTES has been extensively studied in animal models, with tubal ligation, gallbladder surgery, oophorectomy, hysterectomy, gastrojejunostomy, and splenectomy having been described. (Jagannath, S., et al. Peroral transgastric endoscopic ligation of fallopian tubes with long-term survival in a porcine model. Gastrointest. Endosc. 61: 449-453 2005; Experimental studies of transgastric gallbladder surgery: cholecystectomy and cholecystogastric anastomosis. Gastrointest. Endosc. 61: 601-606 2005; Wagh, M. et al., Survival studies after endoscopic transgastric oophorectomy and tubectomy in a porcine model. Gastrointest. Endosc. 63: 473-478 2008; Merrifield, B., et al. Peroral transgastric organ resection: a feasibility study in pigs. Gastrointest. Endosc. 63: 693-697 2006; Kantsevoy, S., et al. Transgastric endoscopic splenectomy: is it possible? Surg. Endosc. 20: 522-525 2006). These surgical procedures are promising advances, due to the potential to eliminate traditional surgical complications, like postoperative abdominal wall pain, wound infections, hernias, adhesions, and impaired immune function. (Wagh, M., Thompson, C. Surgery insight: natural orifice transluminal endoscopic surgery—an analysis of work to date. Gastr. & Hept. 4:7 386-392 2007). Further, NOTES procedures may be performed under conscious sedation and not general anesthesia. (Pearl, J., Ponsky, J., Natural orifice transluminal endoscopic surgery: past present and future. J Min. Acc. Surg. 3:2 43-46 2008). The transluminal approach could be particularly important for morbidly obese patients and others at high risk for standard surgery.

One surgical approach for NOTES involves intercolonic entrance, as the gastric wall and small intestine are relatively sterile. (Hochberger, Lamade, Transgastric surgery in the abdomen: the dawn of a new era, Gastrointestinal Endoscopy; 62(2): 293-296, 2005). In colonic endoscopy procedures, the endoscope must be straight for proper advancement of the endoscope through the colon. Advancing an endoscope through the colon is difficult due to a loop in the sigmoid colon and another at the transverse colon, and often results in a loop formation along the shaft of the scope. As known to those skilled in the art, failure to substantially straighten the loop in the sigmoid colon prior to continuing to advance the scope can cause enlargement of the loop, resulting in more difficulty in advancing the scope and patient pain and injury.

As is well known, over-tubes are not easy to use and can cause complications such as perforation. Moreover, surgical instruments, such as needle scalpels, present hazards to internal organs.

SUMMARY OF THE INVENTION

Despite the prevalence of specially configured endoscopes and splints to reduce sigmoid looping in order to improve the effectiveness and reduce the pain of colonic procedures, such as colonoscopy or NOTES, many operators still face significant difficulty and, on occasion, are unable to reach the small intestine due to looping of the sigmoid. As a result, therefore, what is needed is a device and a method of using that device that improves the use of an endoscope during a surgery by reducing the problems associated with insertion and advancement of the endoscope and instruments through the colon.

Colonic gastrointestinal access of endoscopic instruments has unique problems not addressed with typical endoscopic procedures and instruments. A flexible over-tube of sufficient length to extend from the anus to proximal colon is disclosed herein. The device may be used intraluminally or advanced through the colonic wall and into the peritoneum. The over-tube sheaths and protects the colon throughout the procedure and may guide both a double channel gastroscope or a colonoscope as well as various other instruments through the colon and out the colonic wall into the peritoneum. The device avoids reintubation of the colon, promotes safe and easy access with increased efficiency and accuracy of insertion of the endoscope and other instruments and minimizes the risks of perforation and mucosal injuries and allows secure control of the colostomy.

The over-tube has at least one flexible tube further comprising a proximal end, a distal end, and a longitudinal axis with at least two endoscopic channels. The endoscopic channels are located in the flexible tube, defining a first working channel and a second working channel. The working channels may be both located in one flexible tube, or dispersed in multiple flexible tubes so that each tube comprising at least one working channel. In certain embodiments, a plurality of flexible tubes is fused together. Specifically, a first fused tube is fused to a second fused tube along the longitudinal axis of the tubes. In other embodiments, additional tubes are also fused to the first and second tubes along the respective longitudinal axis of each tube.

The over-tube is of sufficient size that the over-tube extends from the anus, up the proximal colon, and may extend through the colonic wall into the peritoneum. Overtube lengths vary, but preferably are in 25, 50, 75, and 100 cm lengths. The over-tube has a length ranging from 25 to 100 cm in specific embodiments. The first fused tube has an outer diameter of between 8 to 12.6 mm in some embodiments of the invention. The first fused tube may further include an inner diameter of between 2.8-3.8 mm. The over-tube has an additional 10-12 mm channel. This channel is useful for inserting surgical instruments which move in tandem with the endoscope.

The over-tube may be constructed of polyurethane, polyvinyl chloride, polytetrafluoroethylene, polyester, para-phenylenediamine and terephthaloyl chloride polymer, carbon fiber, meta-phenylenediamine and terephthaloyl chloride polymer, nylon, rubber, latex, silicone, polyisoprene, polystyrene and polybutadiene polymer, urethane, polyethylene, polyisoprene, ethylene propylene diene monomer, neoprene, polyurethane, polyvinyl chloride, and styrene butadiene.

The tip of the over-tube is circumscribed by two narrowed inflatable balloons that are utilized on either side of the colostomy to keep the device in place with its lumen open into the peritoneum. A series of ring-shaped balloons are disposed on the distal end of the tube. Specific embodiments use two balloons at a distance such that the balloons fit on either side the colonic wall of a patient. In such embodiments, the balloons are placed on either side of the colonic wall of a patient and inflated, thereby pinning the distal end of the tube to the colonic wall. The over-tube may also include a ring-shaped balloon is disposed on the proximal end of the tube. In such embodiments, the balloon is placed proximal to the rectum and inflated, thereby pinning the proximal end of the tube to the patient's rectum.

In specific embodiments, the distal end of the flexible tube or tubes is tapered, rounded, or adapted to accept a rounded mountable tip. The exterior surface of the flexible tube or tubes is smooth in certain embodiments. These alterations have the advantage of providing additional patient comfort during advancement and removal of the over-tube.

The device has a valve at the distal opening to prevent leakage of peritoneal insufflation. The valve is at least one seal disposed in the lumen of the at least one flexible tube. In specific embodiments, the seals are affixed to the proximal end of the flexible tube. Further, the instrument seals may be made of one or more flexible compounds such as polyester, para-phenylenediamine and terephthaloyl chloride polymer, carbon fiber, expanded PTFE, meta-phenylenediamine and terephthaloyl chloride polymer, nylon, fiber glass, cotton, polypropylene and ceramic, rubber, latex, silicone, polyurethane, polyisoprene, polystyrene and polybutadiene polymer, urethane, polyethylene, polyisoprene, polyvinylchloride, ethylene propylene diene monomer, neoprene, and styrene butadiene. The seals may also be is coated a lubricant. Exemplary lubricants include hydrophilic polymer coatings, Teflon, thermoplastic, cyanoacrylate, parylene, plasma surface treatments, cornstarch powder, silicone oil, silicone grease, astroglide lubricants, mineral oil, glycerin, alcohol, saline, Teflon lubricants, Krytox lubricants, molybdenum disulfide lubricants, and graphite. However, other lubricants known in the art may be used.

The over-tube may also include a stiffened region disposed along the longitudinal axis of the flexible tube or tubes, and may be 10 cm long. The length of the stiffened region may be varied, depending on the usage of the over-tube and patient anatomy. The stiffened region is constructed of any flexible material known in the art, such as polyester, para-phenylenediamine and terephthaloyl chloride polymer, carbon fiber, expanded PTFE, meta-phenylenediamine and terephthaloyl chloride polymer, nylon, rubber, latex, silicone, polyurethane, polyisoprene, polystyrene and polybutadiene polymer, urethane, polyethylene, polyisoprene, polyvinylchloride, ethylene propylene diene monomer, neoprene, polyurethane, polyvinyl chloride, and styrene butadiene.

In a specific embodiment, the device allows for receiving and guiding endoscopic instruments into a patient's anus, through the colon, and into the peritoneum. The over-tube has a flexible protective sheath adapted for insertion into the anus through the colon and out in the peritoneum of a patient. It also has a proximal valve that prevents insufflation leakage. The device has a stiffened region that protects the colonic wall of a patient from iatrogenic injury as a duel channel gastroscope or colonoscope or medical instruments are inserted through the sheath and into the patient's lower gastrointestinal tract. The distal end of the over-tube is surrounded by two narrow inflatable balloons that are utilized on either side of the colotomy to keep the device in place with its lumen open into the peritoneum and further prevent leakage of insufflation. The device has two channels. One channel is provided for duel channel gastroscopes and larger medical instruments or single lumen endoscopes, and has an outer diameter ranging between 8.6 mm and 12.6 mm, and channel size of between 2.8 mm and 3.8 mm. The second channel has an outer diameter that ranges between 10 mm and 12 mm. The device is especially useful in NOTES surgeries.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Disclosed is an over-tube, which is useful in performing various medical procedures, such as NOTES surgery utilizing the colon as an entry point. The device may decrease the total physician and support staff time spent on a procedure, resulting in a benefit to the patient's health and overall prognosis as a result of a decrease in potential procedure complications and reduced time under anesthesia. The device may also result in a net revenue increase by decreasing the overall procedure time, reducing potential patient complications, and reducing overall recovery time and associated costs.

As used herein, the term "endoscope" or "scope" is used to refer to an endoscope, laparoscope, sigmoidoscope, proctoscope, colonoscope, or other types of medical endoscopes. As known to those skilled in the art, a typical endoscope generally comprises a connecting tube, a handle and an insertion tube (the part inserted into the patient). In referring to the opposite ends of the scope or the over-tube of the present invention, the "proximal end" refers to that part of the scope or over-tube which is closest to the operator or physician endoscopist (hereinafter collectively referred to as "operator") performing the procedure, and the "distal end" refers to that part of the scope or over-tube farthest from the operator or physician endoscopist. Although medically the rectum is generally not considered to be part of the colon, which includes the sigmoid colon, descending colon, transverse colon and ascending colon, for purposes of this disclosure general references herein to the term "colon" include the rectum.

The term "over-tube" is used to refer to a generally elongated hollow tubular member that is adaptable for receiving a medical instrument, such as an endoscope, therein to facilitate movement of the scope through the colon.

Figure 1:
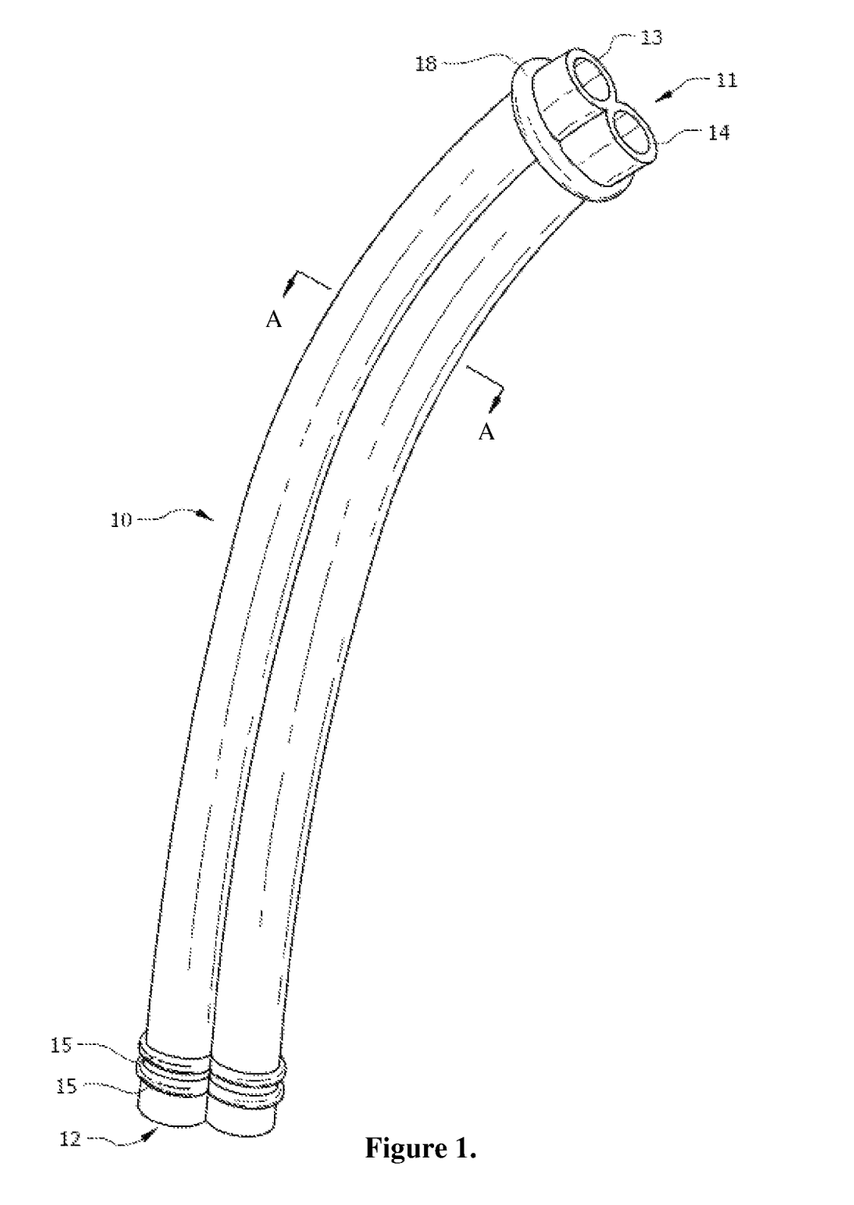
FIG. 1 is a side view of the overtube with two fused working channels.

Endoscopic over-tube 10 is a generally tubular flexible protective sheath comprising a proximal end 11 and a distal end 12. The length of over-tube 10 is in the range of 25-100 centimeters. The over-tube consists of two fused channels, endoscope channel 13 and instrument channel 14, as seen in FIG. 1. Endoscope channel 13 has an outer diameter ranging between 8.0 millimeters and 12.6 millimeters, and channel size of between 2.8 millimeters and 3.8 millimeters. Instrument channel 14 has an outer diameter that ranges between 10 mm and 12 mm. Endoscope channel 13 and instrument channel 14 extend through over-tube 10 and facilitate passing an endoscope through over-tube 10. Distal balloon set 15 comprises a plurality of inflatable balloons disposed on the distal end of the over-tube and adapted to fit on either side of the colostomy. Proximal balloon 18 is disposed on the proximal end of over-tube 10 and is also inflatable.

At least portion of over-tube 10 is laterally flexible, allowing over-tube 10 to flex substantially without kinking during advancement of over-tube 10 through a colon. As illustrated in FIG. 1, over-tube 10 is comprised of a plurality of fused working channels, endoscope channel 13 and instrument channel 14, extending along the entire length of the over-tube 10 from the proximal end 11 to the distal end 12. The fused channel configuration of over-tube 10 allows lateral flexation of the over-tube in one direction, transversely in relation to the fused channel.

Over-tube 10 is suitable for insertion into the rectum and into the colon of a patient and defines a series of fused generally circular or cylindrical bores 16 throughout its length. Bore 16 has a diameter generally in the range of about 5 to about 9 centimeters. Over-tube wall 17 is generally in the range of 3.0 to 10.0 millimeters, seen in FIG. 2.

Over-tube 10 is constructed of a soft flexible material such as polyurethane or polyvinyl chloride. Distal end 12 of over-tube 10 is soft and flexible, allowing for insertion of over-tube 10 along the lumen of the colon and around the sigmoid colon and transverse colon without irritating the colonic peritoneum, seen in FIG. 3. Additionally, distal tip 20 of over-tube 10 may include a tapered portion 21 on both endoscope channel 13 and instrument channel 14. Over-tube 10 may also be constructed of a material which is thermally stable for use in a colon. In this case the thermally stable material used for the over-tube 10 is polytetrafluoroethylene (PTFE). However, over-tube 10 must be constructed of sufficiently pliable material such that over-tube 10 is not overly stiff. Insertion of over-tube 10 into a colon, and navigation of the over-tube through a colon requires flexible or pliable materials to permit a surgeon to utilize the over-tube without undue difficulty and without causing undue discomfort to a patient. However the over-tube must maintain a minimum threshold of stiffness once inserted into the colon to prevent sigmoid loops from reforming as an endoscope or surgical instrument is passed through endoscope channel 13 or instrument channel 14.

Figure 4:
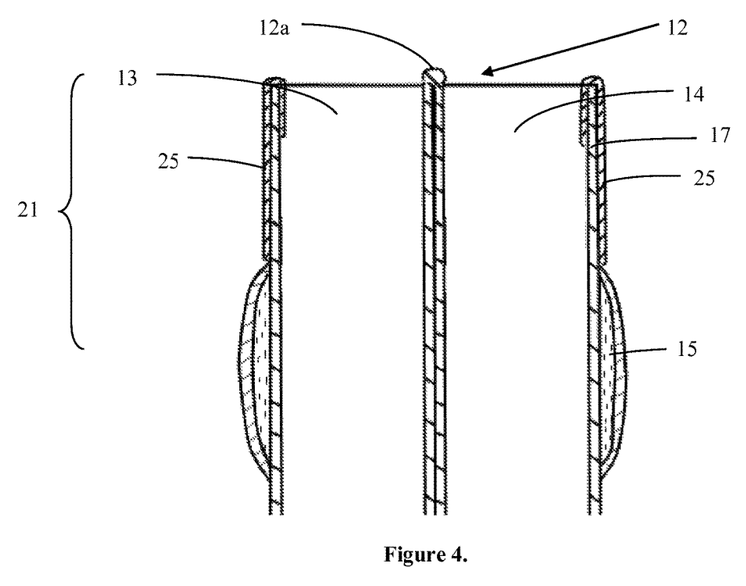
FIG. 4 is a longitudinal section of the overtube depicting the tapered distal end of the present invention. The tapered end is depicted optionally covered in a heat-shrink wrapping to round the distal end.

The thickness of over-tube wall 17 is gradually decreased along tapered portion 21 such that the wall is thinnest at distal end 12 of the over-tube. The reduced wall thickness of over-tube wall 17 makes the distal tip extremely soft and flexible, facilitating advancement of over-tube 10 through the colon. Over-tube 10 utilizes an additional section of heat-shrink tubing 25 fixed to the exterior surface of over-tube 10 at distal end 12 of the over-tube, seen in FIG. 4. Distal end 12 of the heat-shrink tubing is rolled inwardly, and the heat-shrink tubing is positioned around the distal end 3 of the over-tube 10, partially overlapping distal end 12. The heat-shrink tubing is partially inserted into the lumen of the over-tube, such that the heat-shrink tubing extends around the distal end 12 of the over-tube and partially covers the lumen of endoscope channel 13 or instrument channel 14, thereby producing a rounded tip at the distal end 12. Rounded distal end 12a ensures that there are no sharp edges at the distal end of over-tube 10, which prevents traumatic advancement of the over-tube through a colon. Alternatively, distal end 12 may be adapted to accept a rounded mountable tip, such as a compression fitting. The heat-shrink tubing has a smaller diameter than over-tube 10, such that the heat-shrink tubing is stretched into position around distal end 12. In some embodiments, the distal edge of the heat-shrink tubing is rolled to form a rounded proximal end 12, seen in FIG. 8, and heat is applied to shrink the heat-shrink tubing down onto the over-tube and fix the heat-shrink tubing to the exterior surface of over-tube 10.

Figure 5:
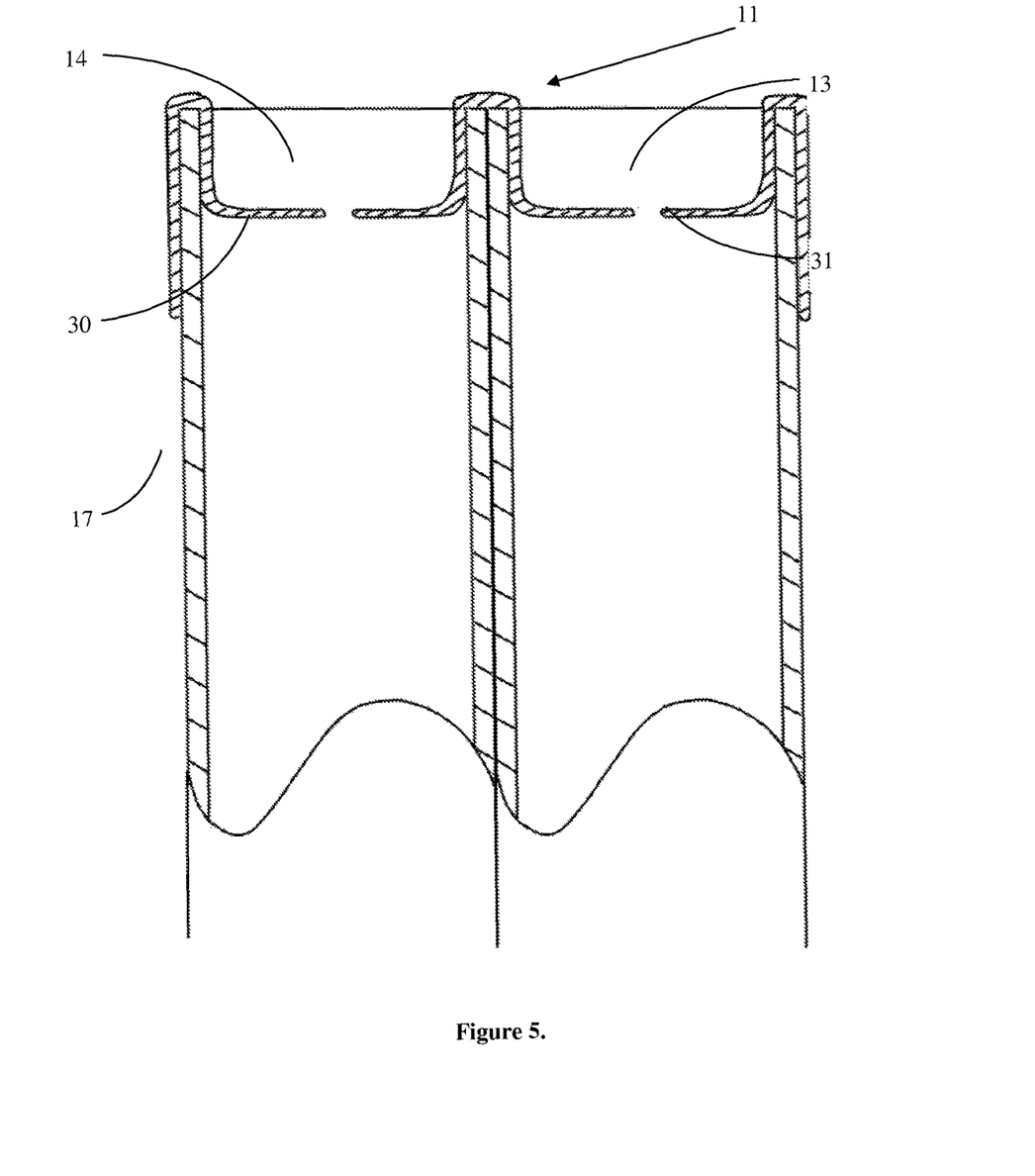
FIG. 5 is a longitudinal section of the overtube depicting the endoscope/instrument seals within the proximal end of the present invention using a diaphragm seal.

Flexible instrument seal 30 and endoscope seal 31 are provided near proximal end 11 of over-tube 10 for sealing between the over-tube 1 and an endoscope or surgical instrument extending through endoscope channel 13 or instrument channel 14, as seen in FIG. 5. Instrument seal 30 and endoscope seal 31 may be constructed of a tubular sheath of film, in this case silicone, material, which is fixed to an exterior surface of the over-tube at proximal end 11 using heat-shrink tubing. As illustrated in FIG. 5, the tubular sheath extends inwardly at the proximal end 11 of the over-tube for sealing between over-tube 10 and an endoscope or surgical instrument, and then proximally to proximal end 11.

The flexible nature of instrument seal 30 and endoscope seal 31 enables the seals to adapt to the size of the endoscope extending through endoscope channel 13. In this manner, a secure, effective seal between the over-tube 10 and an endoscope is achieved regardless of the size diameter range of an endoscope. In addition, the seals possess a low profile, which facilitates easier passage of the endoscope through the over-tube, minimizing discomfort to the patient.

Figure 6:
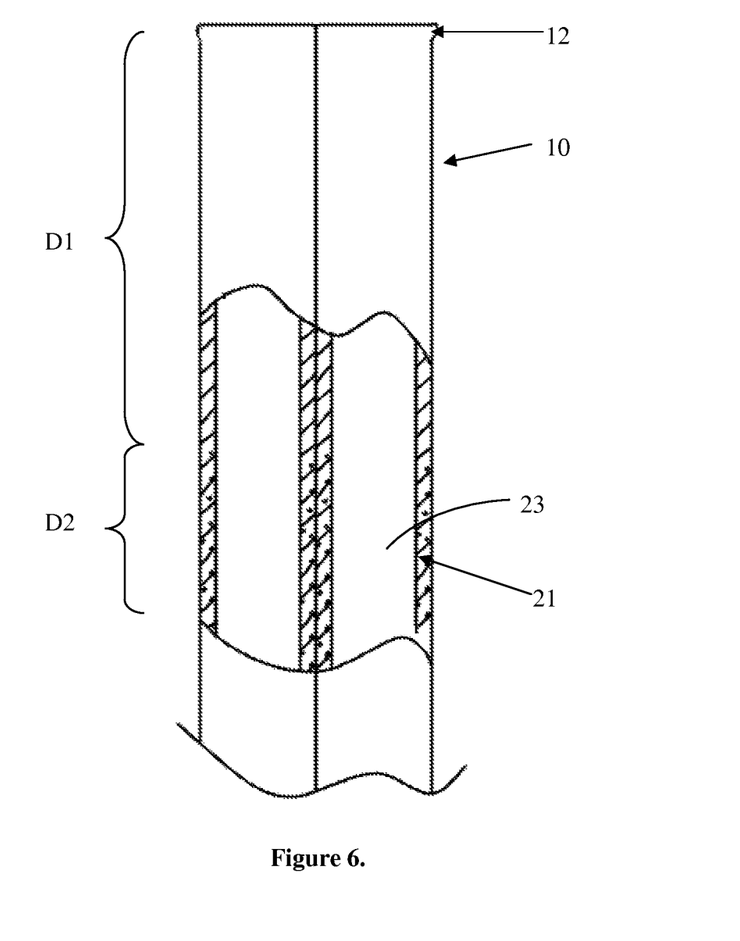
FIG. 6 is a longitudinal section of the overtube of the present invention. Depicted is an embodiment using a stiffened region with support webbing manufactured into the overtube walls.

In some embodiments, stiffened region 21 is provided in over-tube 10, located a first distance D1 from the proximal end of over-tube 10, seen in FIG. 6. The first distance generally equals or approximates the sigmoid loops, approximately 10 centimeters from the proximal end for an average adult patient. From the position defined by D1, the stiffened region 21 extends distally a second distance D2 along the over-tube. Second distance D2 generally equals approximately 10 centimeters for an average patient. However, when adapted for pediatric use, the distance may be varied to complement to physical dimensions of the pediatric patient's colon.

Figure 7:
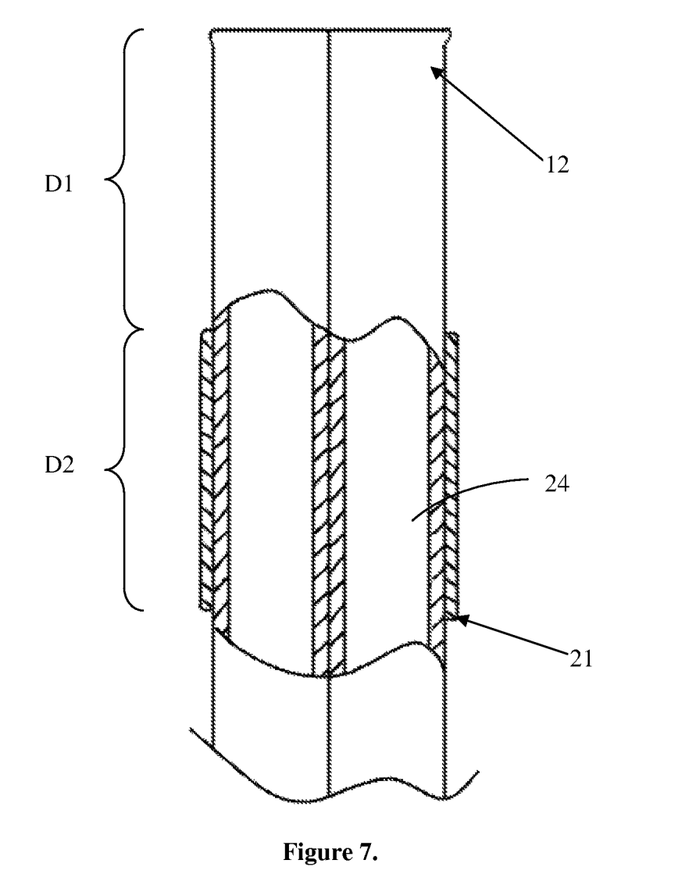
FIG. 7 is a longitudinal section of the overtube of the present invention. Depicted is an embodiment using a stiffened region using a wrapping the outside of the over-tube.

Stiffened region 21 is constructed by wrapping the outside of over-tube 10 with flexible material, such as polyurethane or polyvinyl chloride, or providing heat-shrink wrapping 24, as seen in FIG. 7. The layer provides an increased stiffness and thickness along the portion of the over-tube and generally has a thickness ranging between 1-2 millimeters. The material for stiffened region 21 is affixed to over-tube 10 by conventional fastening techniques such as vulcanization, use of adhesives, hot pressing, etc. Alternatively, stiffened region 21 may be constructed by wrapping the inside of over-tube 10 with the flexible material and affixed to the wall of the over-tube lumen. In another embodiment, the over-tube 10 may be extruded, formed or molded such that the portion of over-tube 10 has a wall thickness greater than the wall thickness of the remainder of over-tube 10, thereby creating stiffened region 21. This type of manufacturing process would eliminate the need for thickening over-tube 10 by affixing flexible material to the over-tube. In other alternate embodiments, stiffened region 21 may be constructed by incorporating longitudinal ribbing 22 within the wall of the portion of over-tube 10 designated by D2.

Figure 2:
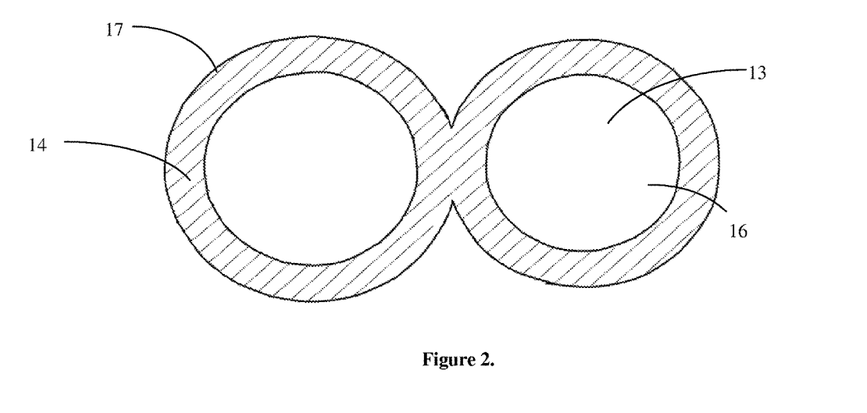
FIG. 2 is a cross section of the overtube at location A-A of FIG. 1. The two fused channels are depicted.

In another alternative embodiment, stiffened region 21 may be generated by providing a stiffer material than the remainder of the over-tube in the region designated by D2. In this construction, stiffened region 21 is attached to the more flexible portions of over-tube 10 by conventional fastening techniques such as vulcanization, use of adhesives, hot pressing, or other techniques known in the art. This construction allows over-tube 10 to have a constant outer and inner diameter throughout its length. Exterior surface 19 of over-tube 10 may be smooth, as seen in FIG. 2, thereby reducing the discomfort and/or pain experienced by the patient during the endoscopy procedure. In some embodiments, support webbing 23 is embedded in over-tube 10, seen in FIG. 6, permitting over-tube 10 to maintain kink-resistant properties. Support webbing 23 may be any suitable form known in the art, such as a mesh, or a braided material. In another alternative the composite over-tube may have a layered construction.

Lubricants may be used to ease insertion of the over-tube into the colon of a patient and/or may be used around the interior on the over-tube lumen to allow ease of passage of the over-tube 10 relative to an endoscope and/or relative to a colon. Exemplary lubricants include silicone or polytetrafluoroethylene (PTFE). Alternatively, the lubricant may be provided as an integral component of the over-tube 10, such as by fixing a silicone coating to the over-tube.

Figure 3:
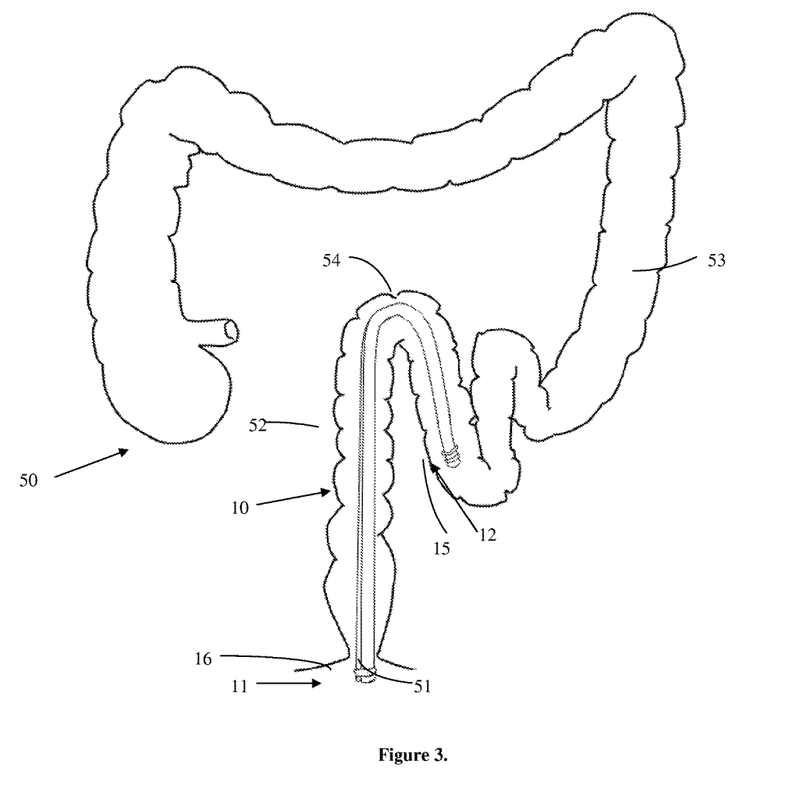
FIG. 3 is a side view of the overtube of the present invention with two working channels. The overtube is depicted inserted in a patient's colon with the distal end advanced to the sigmoid colon.

Over-tube 10 may be inserted into the colon prior to, or concurrently with, an endoscope. Where the over-tube is concurrently inserted, the endoscope is advanced into the one of the plurality of working channels, such as endoscope channel 13, until the endoscope abuts the distal end of over-tube 10. A typical colon 50 is illustrated in FIG. 3, in which rectum 52 leads from anus 51 to sigmoid colon 54. Descending colon 53 leads from sigmoid colon 54 to transverse colon 55. The patient is prepared for surgery, which may include applying a local anesthetic to numb the rectum and to minimize patient discomfort. Distal end 12 of the over-tube 10 is inserted through anus 51 into rectum 52, and the over-tube is advanced into sigmoid colon 54. Because distal end 12 is flexible and rounded it is advanced through the curvature of the colon with minimal discomfort. As the over-tube advances through sigmoid colon 54, a loop may form in the sigmoid colon, which results in stretching of the mesentery to which sigmoid colon 54 is attached. When distal end 12 of over-tube 10 reaches the proximal end of descending colon 53, distal end 12 may be anchored in descending colon 53, and sigmoid colon 54 is straightened by manipulating the over-tube, for example by rotating the over-tube 90 degrees. When the sigmoid colon has been straightened, the anchor is released. Alternatively, the over-tube is rotated in descending colon 53 without anchoring.

Figure 8:
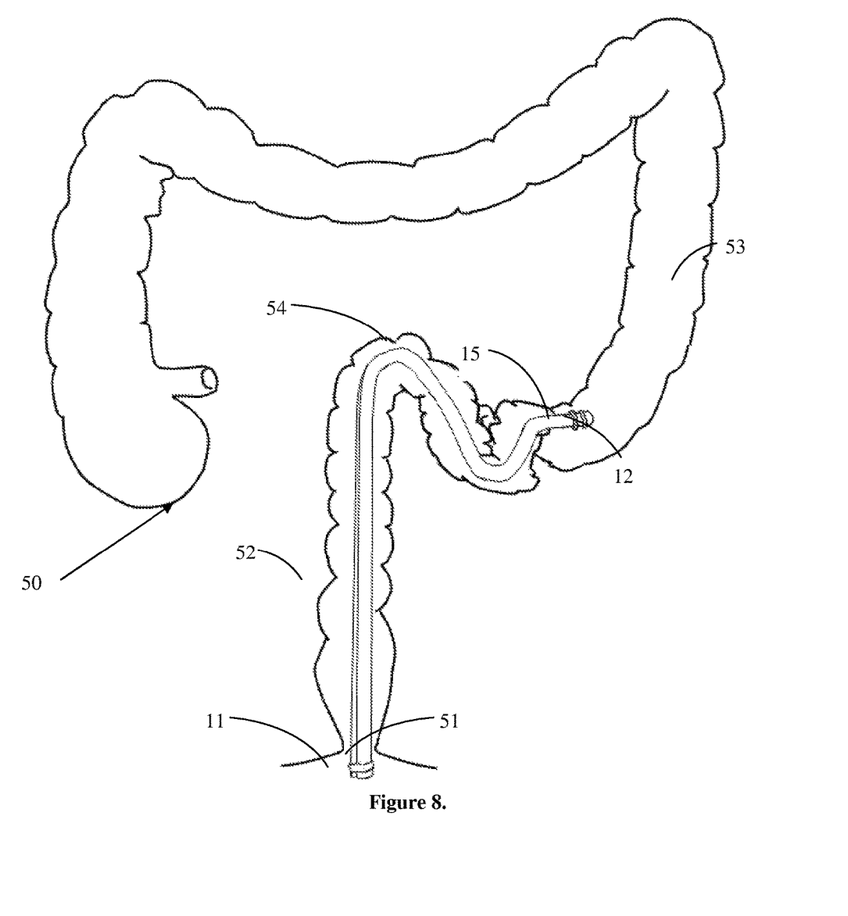
FIG. 8 is an illustration of the overtube inserted in a patient's colon with the distal end advanced through the sigmoid colon, straightening the colon to allow easier passage of endoscopes and instruments through the overtube working channels.

With over-tube 10 extended through the straightened sigmoid colon 54, seen in FIG. 8, the endoscope may then be advanced further through the descending colon 53 and into transverse colon 55. The over-tube acts as a splint to maintain the sigmoid colon in the straightened configuration and ensures that further advancement of the endoscope through the descending colon and into the transverse colon is possible by preventing loops from reforming in the sigmoid colon. In this manner, over-tube 10 acts as a guide for the endoscope or surgical instrument and minimizes the pain or discomfort experienced by the patient during this procedure.

Over-tube 10 also acts as a sheath between the endoscope or surgical instrument and the colon and prevents shearing off of any parts of the colon wall, or puncturing the colon wall, or any other damage to the interior wall of the colon during advancement or retraction of instruments and endoscopes through the colon. This allows the surgeon to efficiently introduce new instruments to the endoscopic surgical site rapidly and with reduced concern for colon damage. Further, the over-tube includes instrument seal 30 and endoscope seal 31 which seal the lumen of the over-tube and ensure air does not leak through the over-tube, thereby allowing the surgeon to induce and maintain pneumoperitoneum. In embodiments using stiffened region 21, the region is disposed to substantially reside in sigmoid colon 54 during the operation and helps insulates the colon from irritation caused by insertion and retraction of medical instrumentation through the over-tube during surgery.

Figure 9:
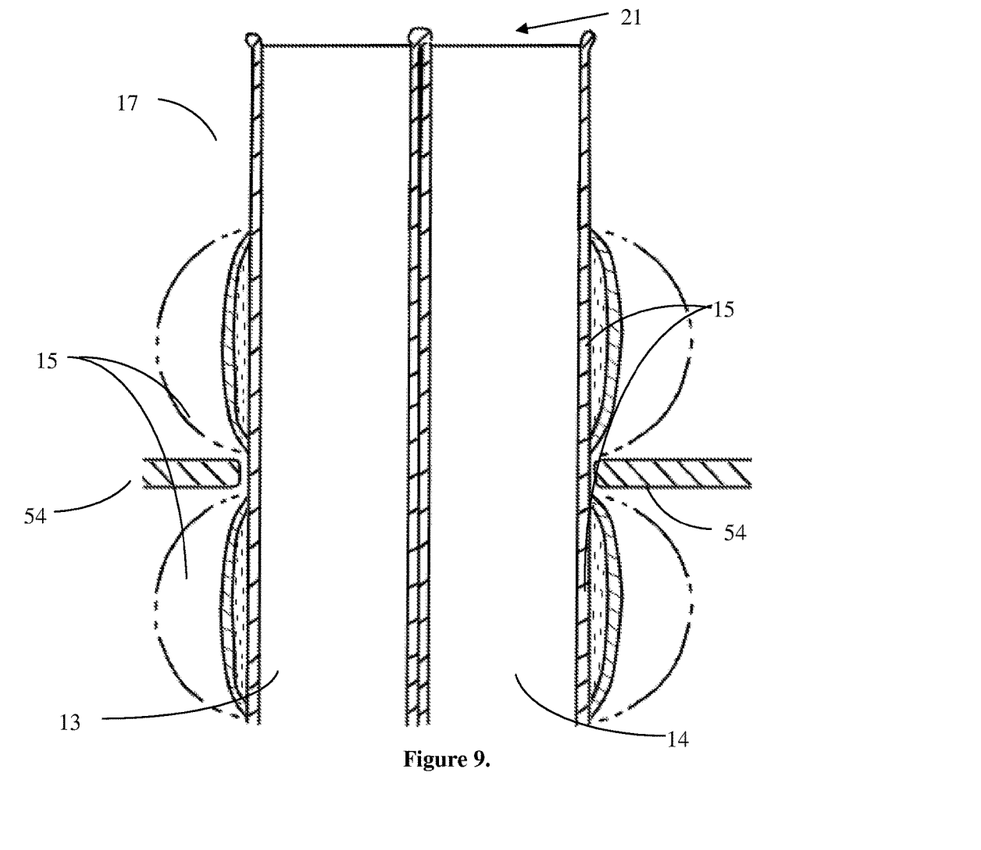
FIG. 9 is an illustration of the overtube inserted in a patient's colon with the distal end advanced to the surgical incision/entry site. Upon incision, the balloons on the distal end of the overtube are moved on either side of the colon wall and inflated to fix the over-tube to the colon and prevent retraction or advancement during surgery.

Upon incision into the colon, over-tube 10 is advanced into the colostomy and positioned such that colon wall 54 is disposed between each distal balloon on distal balloon set 15. Distal balloon set 15 is then inflated, as depicted in FIG. 9, thereby fixing the over-tube to the colon and preventing retraction or advancement of the over-tube during surgery. Proximal balloon 18 is also inflated to fix the proximal end of over-tube 10 during surgery. Medical instrumentation such as endoscopes, evacuation tubes, lavage tubes, etc., is then advanced through cylindrical bores 16 of the over-tube.

During surgery, the endoscope advantageously may be used in conjunction with other surgical instruments. With the endoscope disposed in endoscope channel 13, additional instruments may be quickly and easily passed to access any point in the colon using instrument channel 14, which provides a large working channel through the colon through which any instrument may be advanced. Rapid and less painful exchange of instruments and/or endo scopes is thus facilitated by over-tube 10 because there is no contact between the instruments/endoscopes and the inner wall of the colon during insertion or withdrawal of the instruments/endoscopes. In addition, instrument channel 14 has a much larger diameter than the diameter of a typical endoscope working channel. Thus, larger instruments may be used during a surgical procedure with the over-tube 10. Larger samples may also be removed using the over-tube 10.

After the surgery is completed, the medical instrumentation is removed from over-tube 10. Distal balloon set 15 and proximal balloon 18 are deflated and over-tube 10 is removed from the colon of the patient.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of an endoscopic over-tube, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. An over-tube, comprising
   a plurality of flexible tubes further comprising at least a first and a second flexible tube fused together wherein the plurality of flexible tubes each comprise a proximal end, a distal end, a length extending between the distal and proximal ends, a lateral exterior wall that is fluid impermeable, and a longitudinal axis;
   the lateral exterior wall of the first flexible tube fused to the lateral exterior wall of the second flexible tube along the entire length of the first and second flexible tubes, such that the longitudinal axis of the first flexible tube is laterally spaced and parallel to the longitudinal axis of the second flexible tube;
   the length of each of the plurality of flexible tubes including a proximal section, a distal section and a stiffened section intermediately disposed between the proximal section and the distal section, the proximal section extending from the proximal end to the stiffened section, the stiffened section extending from the proximal section to the distal section, and the distal section extending from the stiffened section to the distal end of the tubes;
   the proximal section having a constant diameter along its length and the distal section having a constant diameter along its length, wherein the constant diameter of the proximal section is equal to the constant diameter of the distal section;
   the stiffened section further includes:
      greater rigidity than the proximal and distal sections;
      stiffening material secured to the lateral exterior walls of the flexible tubes or residing between the lateral exterior wall and a lateral interior walls of each of the plurality of flexible tubes such that an open endoscopic channel in each of the flexible tubes remains unobstructed by the stiffening material;
      a fixed location along the length of the plurality of flexible tubes; and
      an outer diameter adapted to allow the stiffened section to pass into and move throughout a person's body.

2. The over-tube of claim 1, wherein the first flexible tube has an outer diameter of between 8 mm and 12.6 mm.

3. The over-tube of claim 2, wherein the first flexible tube has an inner diameter of between 2.8 mm and 3.8 mm.

4. The over-tube of claim 1, wherein the second flexible tube has an outer diameter of between 10 mm and 12 mm.

5. The over-tube of claim 1, wherein a plurality of ring-shaped balloons are disposed on the distal end of at least one of the plurality of flexible tubes.

6. The over-tube of claim 1, wherein a ring-shaped balloon is disposed on the proximal end of at least one of the plurality of flexible tubes.

7. The over-tube of claim 1, wherein at least one tube is constructed of a material selected from the group consisting of polyurethane, polyvinyl chloride, polytetrafluoroethylene, polyester, para-phenylenediamine and terephthaloyl chloride polymer, carbon fiber, meta-phenylenediamine and terephthaloyl chloride polymer, nylon, rubber, latex, silicone, polyisoprene, polystyrene and polybutadiene polymer, urethane, polyethylene, polyisoprene, ethylene propylene diene monomer, neoprene, polyurethane, polyvinyl chloride, and styrene butadiene.

8. The over-tube of claim 1, wherein the distal end of at least one tube is tapered, rounded, or adapted to accept a rounded mountable tip.

9. The over-tube of claim 1, further comprising a plurality of seals disposed in the lumen of at least one tube.

10. The over-tube of claim 9, wherein the plurality of seals are affixed to the proximal end of at least one tube.

11. The over-tube of claim 9, wherein the plurality of seals comprise at least one compound selected from the group consisting of polyester, para-phenylenediamine and terephthaloyl chloride polymer, carbon fiber, expanded PTFE, meta-phenylenediamine and terephthaloyl chloride polymer, nylon, fiber glass, cotton, polypropylene and ceramic, rubber, latex, polyurethane, polyisoprene, polystyrene and polybutadiene polymer, urethane, polyethylene, polyisoprene, polyvinylchloride, ethylene propylene diene monomer, neoprene, and styrene butadiene.

12. The over-tube of claim 9, wherein the plurality of seals is coated in at least one compound selected from the group consisting of hydrophilic polymer coatings, Teflon, thermoplastic, cyanoacrylate, parylene, plasma surface treatments, cornstarch powder, silicone oil, silicone grease, astroglide lubricants, mineral oil, glycerin, alcohol, saline, Teflon lubricants, Krytox lubricants, molybdenum disulfide lubricants, and graphite.

13. The over-tube of claim 1, wherein the stiffened section is 10 cm long.

14. The over-tube of claim 1, wherein the stiffened section comprises a material selected from the group consisting of polyester, para-phenylenediamine and terephthaloyl chloride polymer, carbon fiber, expanded PTFE, meta-phenylenediamine and terephthaloyl chloride polymer, nylon, rubber, latex, silicone, polyurethane, polyisoprene, polystyrene and polybutadiene polymer, urethane, polyethylene, polyisoprene, polyvinylchloride, ethylene propylene diene monomer, neoprene, polyurethane, polyvinyl chloride, and styrene butadiene.

15. The over-tube of claim 1, wherein the exterior surface of at least one tube is smooth.

16. The over-tube of claim 1, further comprising a valve disposed at the distal end of at least one of the plurality of open endoscopic channels.

17. The over-tube of claim 1, wherein the wall of the first flexible tube and the second flexible tube is between 3.0 mm and 10.0 mm.

18. The over-tube of claim 1, wherein the stiffened section comprises a reinforcement incorporated in the over-tube, wherein the reinforcement is longitudinal ribbing, support webbing, mesh, or braided material.

19. The over-tube of claim 1, wherein the stiffened section is integrated along the longitudinal axis of the plurality of flexible tubes by fusion to the plurality of flexible tubes, vulcanized adhesives, or hot pressing.

20. An endoscopic over-tube, comprising
   a plurality of flexible tubes further comprising at least a first and a second flexible tube fused together wherein the plurality of flexible tubes each comprise a proximal end, a distal end, a length extending between the distal and proximal ends, a lateral exterior wall that is fluid impermeable, and a longitudinal axis;
   the lateral exterior wall of the first flexible tube fused to the lateral exterior wall of the second flexible tube along the entire length of the first and second flexible tubes, such that the longitudinal axis of the first flexible tube is laterally spaced and parallel to the longitudinal axis of the second flexible tube;
   the length of each of the plurality of flexible tubes including a proximal section, a distal section and a stiffened section intermediately disposed between the proximal section and the distal section, the proximal section extending from the proximal end to the stiffened section, the stiffened section extending from the proximal section to the distal section, and the distal section extending from the stiffened section to the distal end;
   the proximal section having a constant diameter along its length and the distal section having a constant diameter along its length, wherein the constant diameter of the proximal section is equal to the constant diameter of the distal section;
   the stiffened section further includes:
     greater rigidity than the proximal and distal sections;
     an outer diameter adapted to allow the stiffened section to pass into and move throughout a person's body; and
   an open endoscopic channel disposed in both the first and second flexible tubes;
   an endoscope having an insertion portion adapted to be inserted into the proximal end of one of the plurality of flexible tubes;
   whereby the over-tube acts as a splint to advance the endoscope into a sigmoid colon, through a descending colon, and into a transverse colon by preventing loops from reforming in the sigmoid colon.

* * * * *